United States Patent
Marui

(10) Patent No.: US 10,278,273 B2
(45) Date of Patent: Apr. 30, 2019

(54) X-RAY GENERATOR AND X-RAY ANALYZER

(71) Applicant: SHIMADZU CORPORATION, Kyoto-shi, Kyoto (JP)

(72) Inventor: Takao Marui, Kyoto (JP)

(73) Assignee: SHIMADZU CORPORATION, Kyoto-shi, Kyoto (JP)

( * ) Notice: Subject to any disclaimer, the term of this patent is extended or adjusted under 35 U.S.C. 154(b) by 177 days.

(21) Appl. No.: 15/198,179

(22) Filed: Jun. 30, 2016

(65) Prior Publication Data

US 2018/0007768 A1    Jan. 4, 2018

(51) Int. Cl.
*H05G 1/02*    (2006.01)
*G01N 23/207*    (2018.01)

(52) U.S. Cl.
CPC ......... *H05G 1/025* (2013.01); *G01N 23/2076* (2013.01)

(58) Field of Classification Search
CPC ... G01N 23/2076; H05G 1/025; H01J 35/105; H01J 35/106; H01J 35/12; H01J 2235/12
See application file for complete search history.

(56) References Cited

U.S. PATENT DOCUMENTS

2004/0196959 A1* 10/2004 Weston ............... H05G 1/02
378/141

FOREIGN PATENT DOCUMENTS

JP     08-148293 A     6/1996
JP     2015081783 A  *  4/2015

OTHER PUBLICATIONS

Wikipedia, "Heat pump", (Jun. 18, 2015), Retrieved from the Internet: <URL: https://web.archive.org/web/20150618080608/https://en.wikipedia.org/wiki/Heat_pump#Historical_development>. (Year: 2015).*

* cited by examiner

*Primary Examiner* — Chih-Cheng Kao
(74) *Attorney, Agent, or Firm* — Sughrue Mion, PLLC

(57) ABSTRACT

A heat pump is used to cool an X-ray tube, and waste heat from the heat pump is used to heat a separate part (a spectroscope, for example). As a result, the X-ray tube can be cooled using the heat pump, and the waste heat from the heat pump resulting from the cooling thereof can be used to heat a separate part. In this way, by heating a separate part using the waste heat from the heat pump, it is possible to effectively utilize heat generated from the X-ray tube so as to reduce the power consumption.

14 Claims, 5 Drawing Sheets

X-RAY GENERATOR AND X-RAY ANALYZER

TECHNICAL FIELD

The present invention relates to an X-ray generator for generating X-rays with an X-ray tube; and an X-ray analyzer.

BACKGROUND ART

An X-ray tube used in an X-ray generator is provided with a filament and a target disposed with space between one another, for example. By applying a high voltage between the filament and the target, it is possible to cause thermal electrons discharged from the filament to collide with the target so as to generate X-rays from the target.

In such an X-ray generator, the target generates heat in step with the generation of X-rays, so a mechanism capable of cooling the target using a cooling medium is sometimes used (for example, see Patent Document 1 below). In addition to liquids such as cooling water, gases such as air are also used as cooling mediums. For example, in an X-ray generator which generates X-rays with a few kW of power, a water cooling system for cooling the target using cooling water may be used, and in an X-ray generator which generates X-rays with power up to several 100 W, an air cooling system for cooling the target using air may be used.

FIG. 5 is a schematic diagram illustrating an example of the configuration of an X-ray analyzer provided with a conventional X-ray generator 101. The X-ray generator 101 is provided with an X-ray tube 111, a high-voltage power supply 112, a cooling water circulator 113, and the like.

Power is supplied to the X-ray tube 111 from the high-voltage power supply 112, and a high voltage is applied between a filament and a target, neither of which is illustrated. As a result, thermal electrons discharged from the filament collide with the target, and X-rays are generated from the target. The target, which generates heat in step with the generation of X-rays, is cooled using cooling water circulated within piping 114 by the cooling water circulator 113.

This X-ray analyzer is a fluorescent X-ray analyzer (XRF), which uses a detector 102 to detect fluorescent X-rays generated by irradiating a sample S with X-rays from the X-ray generator 101 so that the sample S can be analyzed based on the detection result. The fluorescent X-rays generated from the sample S are split by a spectroscope 103 comprising a spectroscopic crystal, and the intensities of specific wavelengths are measured with the detector 102.

The spectroscopic characteristics of this spectroscope 103 are dependent on the surface spacing of the spectroscopic crystal, the positional relationship of the spectroscope 103 with respect to the sample S and the detector 102, or the like. Therefore, when the spectroscope 103 expands or contracts based on changes in ambient temperature, there is a risk that the spectroscopic characteristics may change so that analysis cannot be performed with high precision. Therefore, in the example of FIG. 5, the spectroscope 103 can be heated with a heater 104.

Specifically, the heater 104 and a temperature sensor 105 are disposed inside a spectroscopic chamber 106 together with the spectroscope 103, and the temperature inside the spectroscopic chamber 106 is kept constant by controlling the driving of the heater 104 with a temperature controller 107 based on the temperature inside the spectroscopic chamber 106 detected by the temperature sensor 105. As a result, it becomes possible to prevent the spectroscope 103 from expanding or contracting based on changes in ambient temperature, which makes it possible to perform analysis with high precision.

PRIOR ART DOCUMENT

Patent Document

[PATENT DOCUMENT 1] Japanese Unexamined Patent Application Publication H8-148293

SUMMARY OF THE INVENTION

Problem to be Solved by the Invention

With a conventional configuration such as that described above, heat from the X-ray tube 111 is simply wasted in the cooling water circulator 113, and the spectroscopic chamber 106 is heated by the heater 104. That is, most of the power supplied to the X-ray tube 111 from the high-voltage power supply 112 is converted to heat by the target at the time of the generation of X-rays, and it is also necessary to supply power to the heater 104 in spite of the heat being exhausted via the cooling water circulator 113, which leads to a problem in that the power consumption is large.

The present invention was conceived in light of the circumstances described above, and an object of the present invention is to provide an X-ray generator and an X-ray analyzer capable of reducing power consumption.

Means for Solving the Problem

The X-ray generator of the present invention is an X-ray generator which generates X-rays with an X-ray tube, wherein a heat pump is used to cool the X-ray tube, and waste heat from the heat pump is used to heat a separate part.

With such a configuration, it is possible to cool the X-ray tube using a heat pump and to use the waste heat from the heat pump resulting from the cooling thereof to heat a separate part. In this way, by heating a separate part using the waste heat from the heat pump, it is possible to effectively utilize heat generated from the X-ray tube so as to reduce the power consumption.

The heat pump may be provided with an evaporator for cooling the X-ray tube and a radiator for heating the separate part with the waste heat. In this case, the radiator may be provided in a compartment where the separate part is disposed, and air inside the compartment may be heated by the radiator. In addition, the X-ray generator may also be provided with a temperature sensor for detecting the temperature of the separate part and a temperature control part for adjusting the temperature of the separate part based on a detection signal from the temperature sensor.

The X-ray generator may also be provided with a heater for heating the separate part. In this case, the temperature control part may adjust the temperature of the separate part by controlling the driving of the heater.

With such a configuration, the temperature of the separate part can be adjusted by simply heating slightly with the heater while utilizing the waste heat from the heat pump to heat the separate part, so the power consumption can be reduced effectively.

The X-ray generator may also be provided with an opening mechanism for adjusting the circulation of air between the inside and outside of the compartment. In this case, the temperature control part may adjust the temperature of the separate part by controlling the driving of the opening mechanism.

With such a configuration, the temperature of the separate part can be adjusted by simply cooling slightly with the air from the opening mechanism while utilizing the waste heat from the heat pump to heat the separate part, so the power consumption can be reduced effectively.

The X-ray generator may also be provided with an air conditioner capable of heating and cooling the separate part. In this case, the temperature control part may adjust the temperature of the separate part by controlling the driving of the air conditioner.

With such a configuration, the temperature of the separate part can be adjusted well by heating or cooling with the air conditioner while utilizing the waste heat from the heat pump to heat the separate part.

The heat pump may be provided with a first radiator and a second radiator, and the separate part may be heated with the waste heat from the first radiator. In this case, the first radiator may be provided inside the compartment, and the second radiator may be provided outside the compartment. In addition, the heat pump may be provided with a flow rate adjustment part for adjusting the ratio of the flow rate of the cooling medium with respect to the first radiator and the second radiator, and the temperature control part may adjust the temperature of the separate part by controlling the driving of the flow rate adjustment part.

With such a configuration, the temperature of the separate part can be adjusted well by adjusting the ratio of the flow rate of the cooling medium with respect to the first radiator and the second radiator with the flow rate adjustment part while utilizing the waste heat from the first radiator to heat the separate part.

The X-ray generator may also be provided with a high-voltage power supply for supplying power to the X-ray tube and a heat pump control part for controlling the driving of the heat pump based on the amount of power supplied to the X-ray tube from the high-voltage power supply.

With such a configuration, the driving of the heat pump can be controlled by determining the amount of driving of the heat pump required to cool the X-ray tube based on the amount of power supplied to the X-ray tube from the high-voltage power supply, which makes it possible to simplify the configuration in comparison to a configuration in which the driving of the heat pump is controlled by detecting the temperature of the X-ray tube.

The X-ray analyzer of the present invention analyzes a sample using X-rays generated by the X-ray generator.

With such a configuration, when analyzing a sample using X-rays generated by the X-ray generator, it is possible to cool the X-ray tube using a heat pump and to use the waste heat from the heat pump resulting from the cooling thereof to heat a separate part. In this way, by heating a separate part using the waste heat from the heat pump, it is possible to effectively utilize heat generated from the X-ray tube so as to reduce the power consumption.

The X-ray analyzer may also be provided with a spectroscope for splitting light from the sample. In this case, the X-ray analyzer preferably uses the waste heat from the heat pump to heat the spectroscope.

With such a configuration, it is possible to heat the spectroscope using the waste heat from the heat pump. At this time, by adjusting the temperature of the spectroscope to a constant level, it is possible to prevent the spectroscopic characteristics from changing as the spectroscope expands or contracts due to heat, which makes it possible to perform analysis with high precision.

Effect of the Invention

With the present invention, by heating a separate part using waste heat from the heat pump, it is possible to effectively utilize heat generated from the X-ray tube to reduce the power consumption.

MODES FOR CARRYING OUT THE INVENTION

Figure 1:
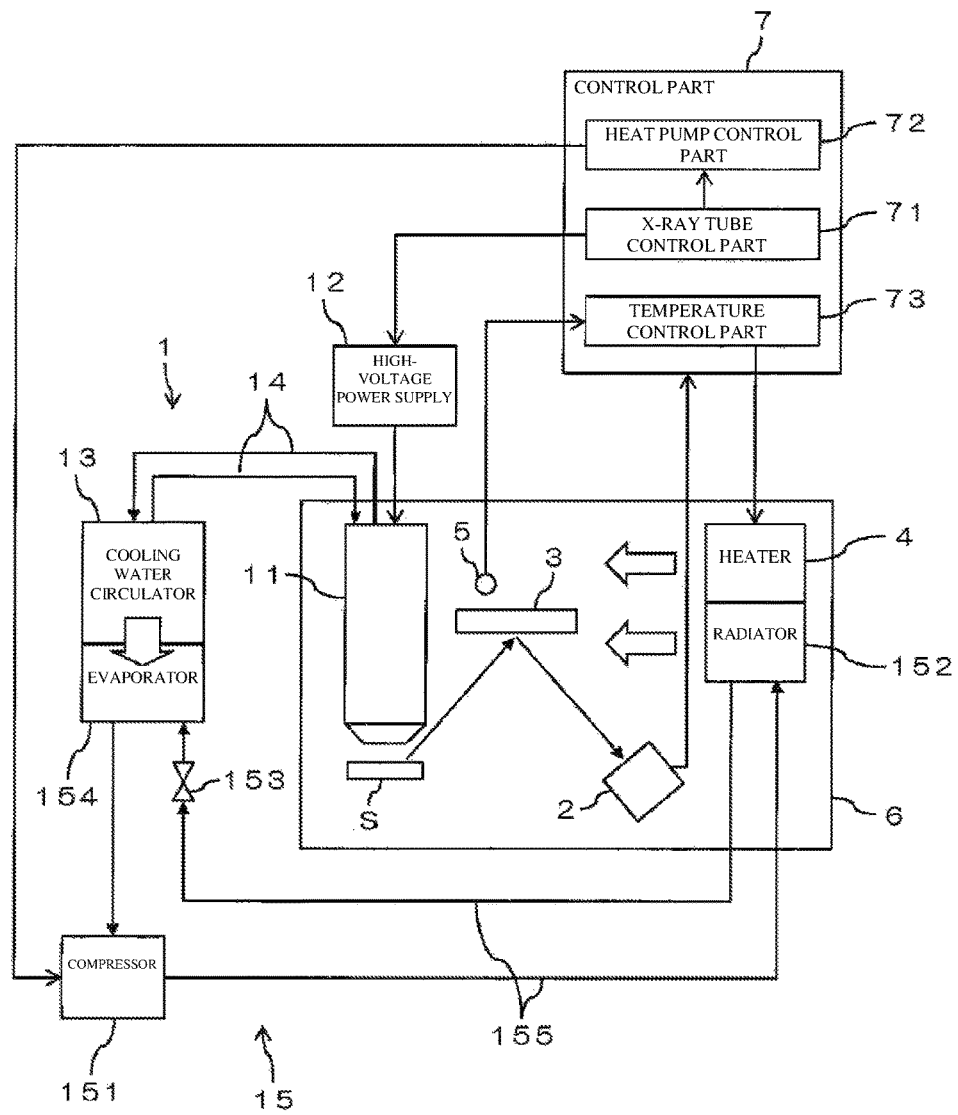
FIG. 1 is a schematic diagram illustrating an example of the configuration of an X-ray analyzer provided with the X-ray generator of a first embodiment of the present invention.

FIG. 1 is a schematic diagram illustrating an example of the configuration of an X-ray analyzer provided with an X-ray generator 1 of a first embodiment of the present invention. The X-ray generator 1 is provided with an X-ray tube 11, a high-voltage power supply 12, a cooling water circulator 13, and the like.

The X-ray tube 11 is provided with a filament and a target (neither of which is illustrated) disposed with space between one another, for example. The target can be formed from Cu, Cr, Mo, Al, Ag, or Au, for example. Power is supplied to the X-ray tube 11 from the high-voltage power supply 12, and a high-voltage of about 50 kV, for example, is applied between the filament and the target as a tube voltage. As a result, thermal electrons are discharged from the filament toward the target, and the thermal electrons collide with the target so that X-rays are generated.

The target generates heat when X-rays are generated, so the target (X-ray tube 11) is cooled using a cooling water circulator 13. Specifically, the X-ray tube 11 and the cooling water circulator 13 are connected via a piping 14, and by driving the cooling water circulator 13, it becomes possible to circulate cooling water (purified water, for example) within the X-ray tube 11 so as to cool the target.

The X-ray generator 1 in this embodiment is provided with a heat pump 15 for cooling the cooling water that has been heated by the heat of the target. By using the heat pump 15 to cool the cooling water circulated by the cooling water circulator 13, it is possible to use the heat pump 15 to cool the X-ray tube 11.

The heat pump 15 is provided with a compressor 151, a radiator 152, an expansion valve 153, and an evaporator 154, and these are connected in a ring shape using a piping 155 so that a cooling medium can be circulated via the piping 155. The cooling medium is compressed by the compressor 151 to form a high-temperature, high-pressure gas and is then radiated by the radiator 152 to form a high-temperature, high-pressure liquid. The cooling medium is then expanded with the expansion valve 153 to form a low-temperature, low-pressure liquid, and the cooling medium then becomes a low-temperature, low-pressure gas due to heat exchange with the evaporator 154 and is fed once again to the compressor 151.

The evaporator 154 performs heat exchange by absorbing heat from the cooling water circulated by the cooling water circulator 13 and cools the X-ray tube 11 via the cooling water. In this case, it is possible to use a configuration in which the evaporator 154 is brought into contact with the cooling water circulated by the cooling water circulator 13, for example. However, the present invention is not limited to such a configuration, and various other configurations can be used as long as the configurations enable the cooling of the X-ray tube 11 with the evaporator 154.

The X-rays generated by the X-ray generator 1 are used to analyze a sample S. The X-ray analyzer in this embodiment is a fluorescent X-ray analyzer (XRF), which performs analysis by detecting fluorescent X-rays generated by irradiating the sample S with X-rays from the X-ray generator 1, for example, and is provided with a detector 2, a spectroscope 3, a heater 4, a temperature sensor 5, and the like.

This X-ray analyzer is a so-called wavelength dispersion-type fluorescent X-ray analyzer, wherein fluorescent X-rays generated from the sample S are split by the spectroscope 3 comprising a spectroscopic crystal. By then detecting the split fluorescent X-rays with the detector 2, the intensities of specific wavelengths can be measured. The detector 2 and the spectroscope 3 are disposed inside a spectroscopic chamber 6 in which the sample S is housed. The spectroscopic chamber 6 is a compartment partitioned by a wall surface so that the circulation of air is controlled between the inside and outside of the spectroscopic chamber 6.

The spectroscopic characteristics of this spectroscope 3 are dependent on the surface spacing of the spectroscopic crystal, the positional relationship of the spectroscope 3 with respect to the sample S and the detector 2, or the like. Therefore, when the spectroscope 3 expands or contracts based on changes in ambient temperature, there is a risk that the spectroscopic characteristics may change so that analysis cannot be performed with high precision. Therefore, in this embodiment, the spectroscope 3 can be heated with the heater 4, and the temperature of the spectroscope 3 can be detected with the temperature sensor 5.

The heater 4 and the temperature sensor 5 are disposed inside the spectroscopic chamber 6, and the spectroscope 3 can be heated by heating the air inside the spectroscopic chamber 6 with the heater 4, while the temperature of the spectroscope 3 can be detected by detecting the temperature of the air inside the spectroscopic chamber 6 with the temperature sensor 5. However, the present invention is not limited to such a configuration, and the configuration may also be such that at least one of the heater and the temperature sensor 5 is connected directly to the spectroscope 3 or connected via a thermal conductor.

In this embodiment, the radiator 152 of the heat pump 15 is disposed inside the spectroscopic chamber 6. As a result, it becomes possible to heat the air inside the spectroscopic chamber 6 with waste heat from the radiator 152 so as to heat the spectroscope 3. That is, the waste heat from the heat pump 15 can be used to heat the spectroscope 3. The radiator 152 is preferably disposed near the heater 4, and the configuration may also be such that the heater is connected directly to the spectroscope 3 or connected via a thermal conductor.

As described above, in this embodiment, the X-ray tube 11 can be cooled using the heat pump 15, and the waste heat from the heat pump 15 (radiator 152) resulting from the cooling thereof can be used to heat the spectroscope 3. In this way, by heating the spectroscope 3 using the waste heat from the heat pump 15, it is possible to effectively utilize heat generated from the X-ray tube 11 so as to reduce the power consumption.

The operation of this X-ray analyzer is controlled by a control part 7. The control part 7 is a structure including a CPU (Central Processing Unit), for example, and the CPU executes programs so as to function as an X-ray tube control part 71, a heat pump control part 72, a temperature control part 73, and the like.

The X-ray tube control part 71 controls the amount of power supplied to the X-ray tube 11 from the high-voltage power supply 12 so that a tube voltage determined by the analysis conditions is applied to the X-ray tube 11. Accordingly, the amount of heat generated in the X-ray tube 11 fluctuates depending on the analysis conditions, and the temperature of the cooling water in the cooling water circulator 13 also fluctuates correspondingly.

The heat pump control part 72 controls the driving of the heat pump 15 by controlling the operation of the compressor 151 of the heat pump 15. In this embodiment, the amount of power supplied to the X-ray tube 11 is determined by the X-ray tube control part 71, and the heat pump control part 72 controls the driving of the heat pump 15 based on this amount of power. That is, the driving of the heat pump 15 is controlled by determining the amount of driving of the heat pump 15 required to cool the X-ray tube 11 based on the amount of power supplied to the X-ray tube 11, which makes it possible to simplify the configuration in comparison to a configuration in which the driving of the heat pump 15 is controlled by detecting the temperature of the X-raytube 11.

The temperature control part 73 adjusts the temperature of the spectroscope 3 by controlling the driving of the heater 4 based on a detection signal from the temperature sensor 5. Specifically, the temperature of the spectroscope 3 is set to be slightly lower than the target value with the waste heat from the heat pump 15 alone, and the temperature control part 73 adjusts the amount of heating by the heater 4 so that the temperature of the spectroscope 3 can be made close to the target value.

As a result, the temperature of the spectroscope 3 can be adjusted by simply heating slightly with the heater 4 while utilizing the waste heat from the heat pump 15 to heat the spectroscope 3, so the power consumption can be reduced effectively. At this time, when the temperature of the spectroscope 3 is adjusted to a constant level, it is possible to prevent the spectroscopic characteristics from changing as a result of the spectroscope 3 expanding or contracting due to heat, which makes it possible to perform analysis with high precision.

However, the control part 7 can also determine the amount of driving of the heat pump 15 required to cool the X-ray tube 11 based on the amount of power supplied to the X-ray tube 11 and can also estimate the amount of waste heat from the radiator 152 based on the amount of driving of the heat pump 15. In this case, the temperature sensor 5 can be omitted by using a configuration in which the temperature control part 73 controls the driving of the heater 4 based on the estimated amount of waste heat from the radiator 152.

Figure 2:
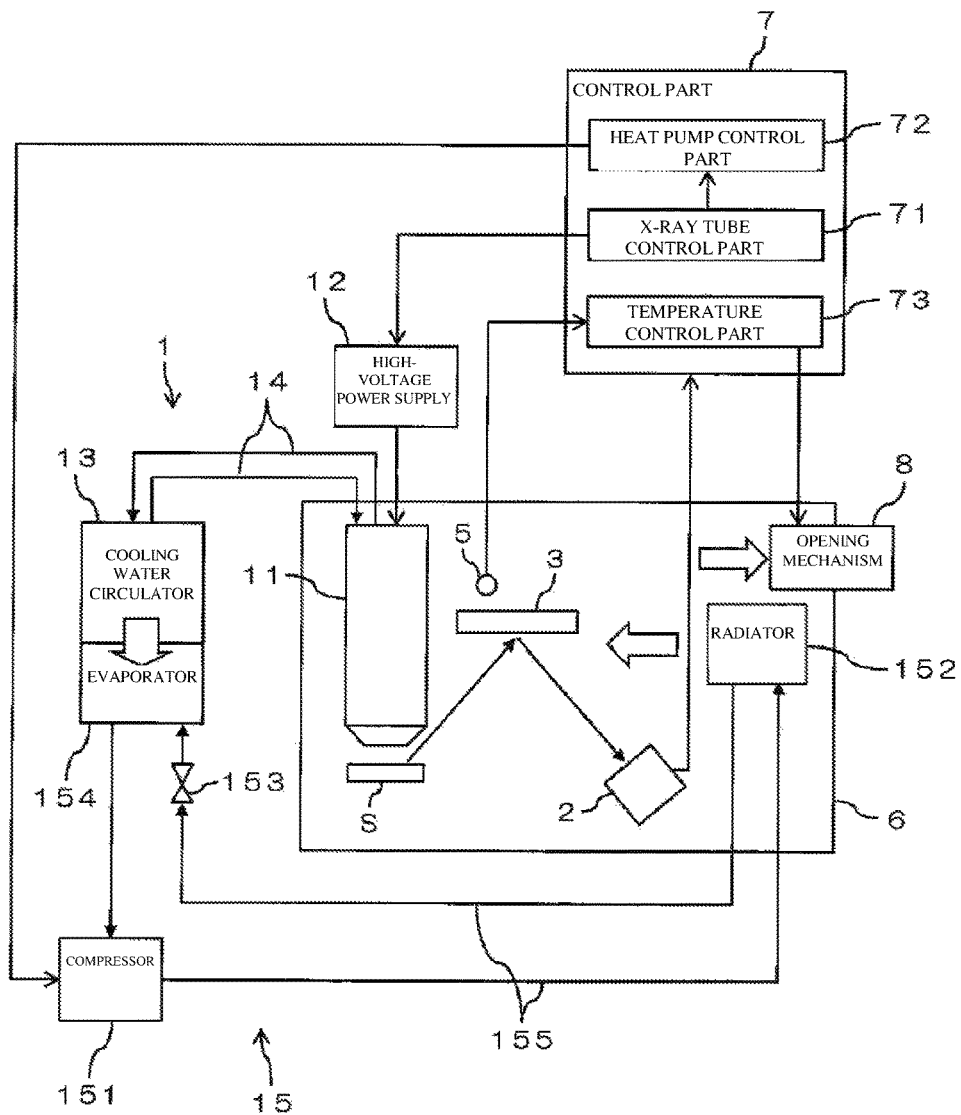
FIG. 2 is a schematic diagram illustrating an example of the configuration of an X-ray analyzer provided with the X-ray generator of a second embodiment of the present invention.

FIG. 2 is a schematic diagram illustrating an example of the configuration of an X-ray analyzer provided with an X-ray generator 1 of a second embodiment of the present invention. The X-ray analyzer of this embodiment differs from the first embodiment described above in that it is not provided with a heater 4 but is provided with an opening mechanism 8. In this embodiment, configurations that are the same as those of the first embodiment described above are labeled with the same symbols in the drawing, and detailed explanations thereof will be omitted.

In this embodiment as well, as in the first embodiment described above, the X-ray tube 11 can be cooled using the heat pump 15, and the waste heat from the heat pump 15 (radiator 152) caused by the cooling thereof can be used to heat the spectroscope 3. In this way, by heating the spectroscope 3 using the waste heat from the heat pump 15, it is possible to effectively utilize heat generated from the X-ray tube 11 so as to reduce the power consumption.

The opening mechanism 8 can adjust the circulation of air between the inside and outside of the spectroscopic chamber 6 by opening and closing an opening (not illustrated) provided in a section of the wall surface of the spectroscopic chamber 6, for example. The temperature control part 73 adjusts the temperature of the spectroscope 3 by controlling the driving of the opening mechanism 8 based on the detection signal from the temperature sensor 5. Specifically, the temperature of the spectroscope 3 is set to be slightly higher than the target value with the waste heat from the heat pump 15 alone, and the temperature control part 73 adjusts the amount of air flowing in from the opening mechanism 8 so that the temperature of the spectroscope 3 can be made close to the target value.

As a result, the temperature of the spectroscope 3 can be adjusted by simply cooling slightly with the air from the opening mechanism 8 while utilizing the waste heat from the heat pump 15 to heat the spectroscope 3, so the power consumption can be reduced effectively. At this time, when the temperature of the spectroscope 3 is adjusted to a constant level, it is possible to prevent the spectroscopic characteristics from changing as a result of the spectroscope 3 expanding or contracting due to heat, which makes it possible to perform analysis with high precision.

Figure 3:
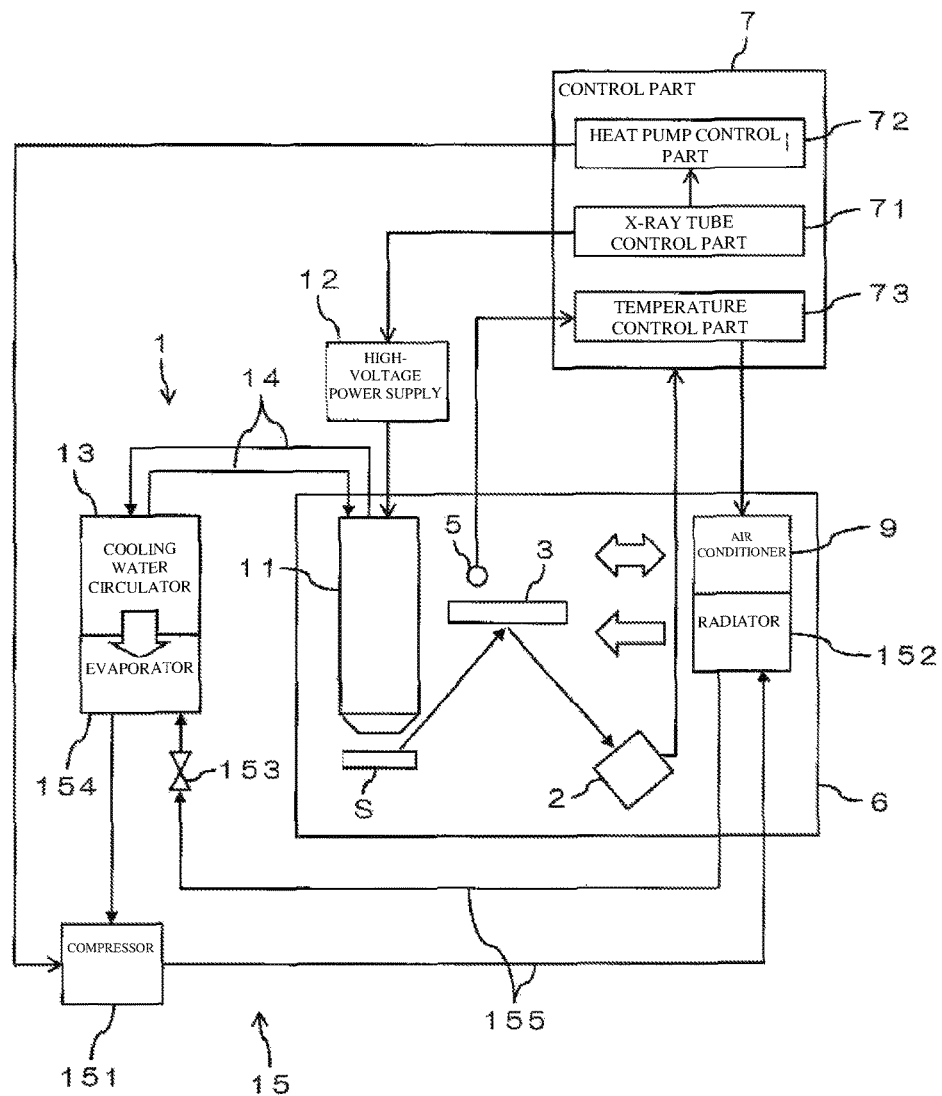
FIG. 3 is a schematic diagram illustrating an example of the configuration of an X-ray analyzer provided with the X-ray generator of a third embodiment of the present invention.

FIG. 3 is a schematic diagram illustrating an example of the configuration of an X-ray analyzer provided with an X-ray generator 1 of a third embodiment of the present invention. The X-ray analyzer of this embodiment differs from the first embodiment described above in that it is not provided with a heater 4 but is provided with an air conditioner 9. In this embodiment, configurations that are the same as those of the first embodiment described above are labeled with the same symbols in the drawing, and detailed explanations thereof will be omitted.

In this embodiment as well, as in the first embodiment described above, the X-ray tube 11 can be cooled using the heat pump 15, and the waste heat from the heat pump 15 (radiator 152) caused by the cooling thereof can be used to heat the spectroscope 3. In this way, by heating the spectroscope 3 using the waste heat from the heat pump 15, it is possible to effectively utilize heat generated from the X-ray tube 11 so as to reduce the power consumption.

The air conditioner 9 can heat and cool the spectroscope 3 by heating and cooling the air inside the spectroscopic chamber 6. The temperature control part 73 adjusts the temperature of the spectroscope 3 by controlling the driving of the air conditioner 9 based on the detection signal from the temperature sensor 5. Specifically, the temperature control part 73 controls the driving of the air conditioner 9 so that heating is performed by the air conditioner 9 when the temperature of the spectroscope 3 is lower than the target value and so that cooling is performed by the air conditioner 9 when the temperature of the spectroscope 3 is higher than the target value.

As a result, the temperature of the spectroscope 3 can be adjusted well by slightly heating or cooling with the air conditioner 9 while utilizing the waste heat from the heat pump 15 to heat the spectroscope 3. At this time, when the temperature of the spectroscope 3 is adjusted to a constant level, it is possible to prevent the spectroscopic characteristics from changing as a result of the spectroscope 3 expanding or contracting due to heat, which makes it possible to perform analysis with high precision.

Figure 4:
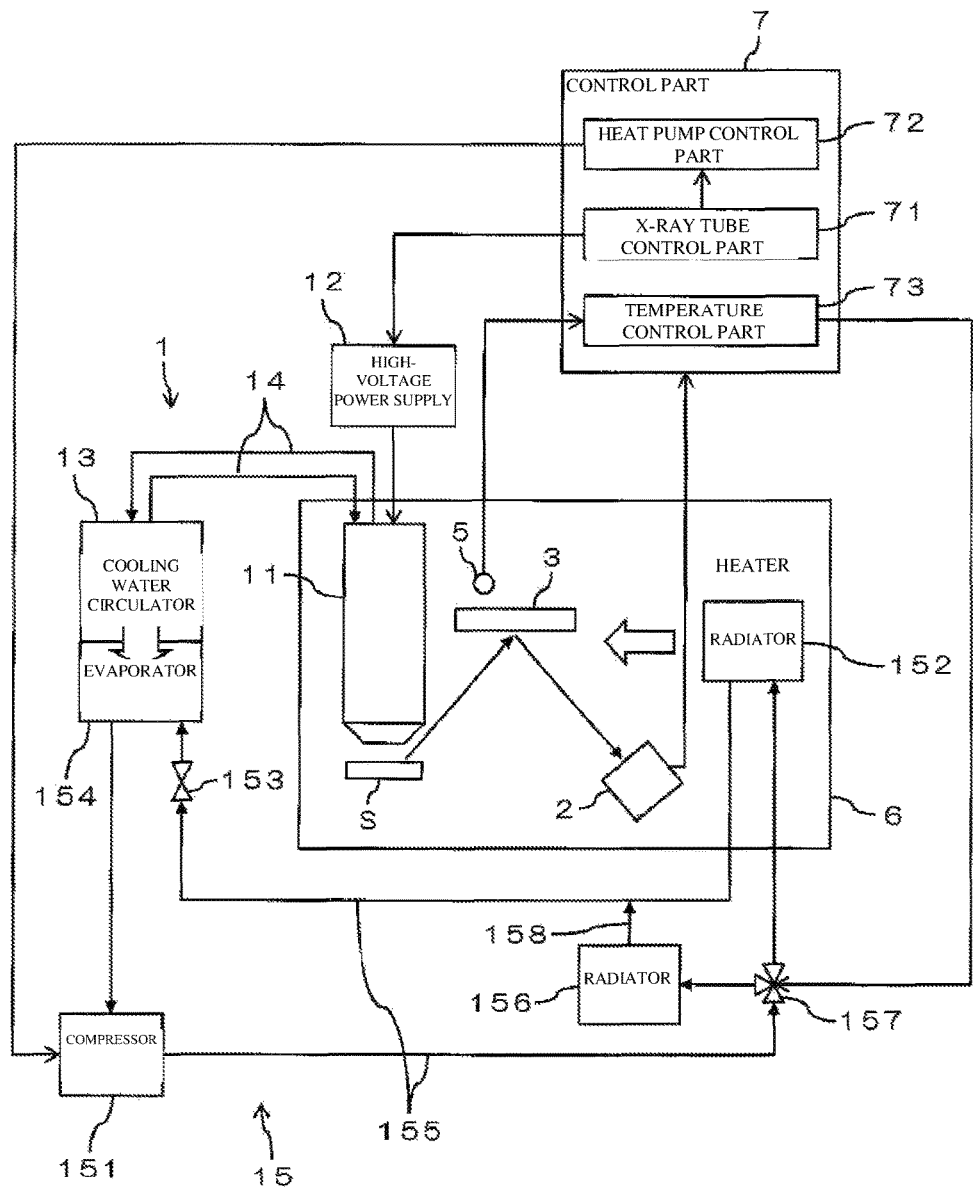
FIG. 4 is a schematic diagram illustrating an example of the configuration of an X-ray analyzer provided with the X-ray generator of a fourth embodiment of the present invention.
Figure 5:
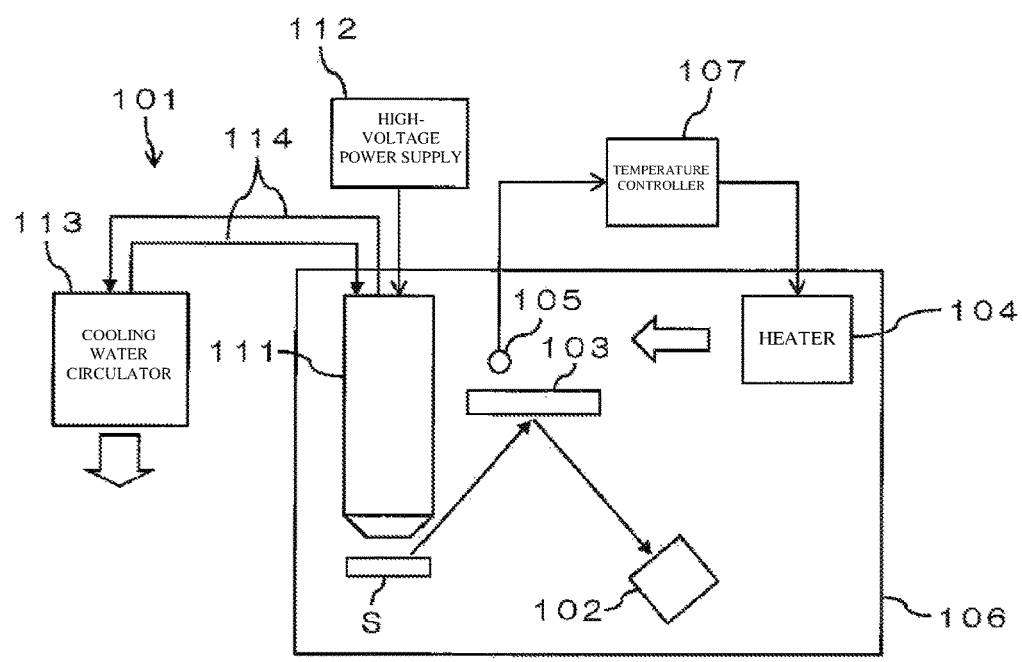
FIG. 5 is a schematic diagram illustrating an example of the configuration of an X-ray analyzer provided with a conventional X-ray generator.

FIG. 4 is a schematic diagram illustrating an example of the configuration of an X-ray analyzer provided with an X-ray generator 1 of a fourth embodiment of the present invention. The X-ray analyzer of this embodiment differs from the first embodiment described above in that it is not provided with a heater 4 but is provided with a second radiator 156. In this embodiment, configurations that are the same as those of the first embodiment described above are labeled with the same symbols in the drawing, and detailed explanations thereof will be omitted.

In the heat pump 15 of this embodiment, a flow rate adjustment part 157 comprising a three-way valve, for example, is provided at an intermediate point along the piping 155 so that some or all of the cooling medium in the piping 155 can be guided to a branch pipe 158. The radiator 156 is provided at an intermediate point along the branch pipe 158, and the ratio of the flow rate of the cooling medium with respect to the radiator 152 (first radiator) and the radiator 156 (second radiator) can be adjusted by adjusting the flow rate into the branch pipe 158 with the flow rate adjustment part 157. Here, the radiator 152 is provided inside the spectroscopic chamber 6, whereas the radiator 156 is provided outside the spectroscopic chamber 6.

In this embodiment as well, as in the first embodiment described above, the X-ray tube 11 can be cooled using the heat pump 15, and the waste heat from the heat pump 15 (radiator 152) caused by the cooling thereof can be used to heat the spectroscope 3. In this way, by heating the spectroscope 3 using the waste heat from the heat pump 15, it is possible to effectively utilize heat generated from the X-ray tube 11 so as to reduce the power consumption.

The temperature control part 73 adjusts the temperature of the spectroscope 3 by controlling the driving of the flow rate adjustment part 157 based on the detection signal from the temperature sensor 5. Specifically, the temperature control part 73 controls the driving of the flow rate adjustment part 157 so that the amount of waste heat from the radiator 152 is increased by increasing the ratio of the flow rate of the cooling medium with respect to the radiator 152 when the temperature of the spectroscope 3 is lower than the target value and so that the amount of waste heat from the radiator 152 is reduced by reducing the ratio of the flow rate of the cooling medium with respect to the radiator 152 when the temperature of the spectroscope 3 is higher than the target value.

As a result, the temperature of the spectroscope 3 can be adjusted well by adjusting the ratio of the flow rate of the cooling medium with respect to the radiator 152 and the radiator 156 with the flow rate adjustment part 157 while utilizing the waste heat from the heat pump 15 (radiator 152) to heat the spectroscope 3. At this time, when the temperature of the spectroscope 3 is adjusted to a constant level, it is possible to prevent the spectroscopic characteristics from changing as a result of the spectroscope 3 expanding or contracting due to heat, which makes it possible to perform analysis with high precision.

Configurations such as those illustrated in the first through fourth embodiments above can be combined as desired. For example, by combining the first embodiment and the second embodiment so as to form a configuration in which the X-ray analyzer is provided with a heater 4 and an opening mechanism 8. That is, heating can be performed by the heater 4 when the temperature of the spectroscope 3 is lower than the target value, and cooling can be performed by the opening mechanism 8 when the temperature of the spectroscope 3 is higher than the target value.

In the embodiments described above, configurations in which the X-ray tube 11 is cooled by the cooling water circulator 13 using cooling water were explained, but the present invention is not limited to cooling water, and the configuration may also be such that the X-ray tube 11 is cooled using a liquid other than water or a gas such as air as a cooling medium. In addition, the present invention is not limited to a configuration provided with a cooling water circulator 13, and the configuration may also be such that the X-ray tube 11 is cooled directly by the heat pump 15 (evaporator 154).

The present invention is not limited to a configuration in which the detector 2, the spectroscope 3, the X-ray tube 11, the radiator 152, and the like are provided inside the spectroscopic chamber 6 in which the sample S is disposed, and the configuration may be such that at least one of the detector 2, the spectroscope 3, the X-ray tube 11 and the radiator 152 is provided in a separate compartment or such that a compartment such as the spectroscopic chamber 6 is omitted.

A plurality of spectroscopes 3 may be provided rather than a single unit. In this case, it is preferable for the configuration to be such that all of the spectroscopes 3 can be heated uniformly by the waste heat from the heat pump 15. In addition, the spectroscope 3 is not limited to X-rays and may also split other forms of light such as visible light or infrared rays.

However, the configuration may be such that a portion other than the spectroscope 3—that is, a portion other than the X-ray tube 11 provided in the X-ray analyzer—or a separate part such as the sample S is heated by the waste heat from the heat pump 15.

The X-ray generator of the present invention is not limited to a wavelength-dispersion-type fluorescent X-ray analyzer and may also be applied to other X-ray analyzers such as an energy dispersion-type fluorescent X-ray analyzer or an X-ray diffractometer (XRD). In addition, the X-ray generator of the present invention is not limited to an X-ray analyzer and may also be applied to various other instruments including medical instruments such as an X-ray device, for example.

EXPLANATION OF REFERENCES

1 X-ray generator
2 detector
3 spectroscope
4 heater
5 temperature sensor
6 spectroscopic chamber
7 control part
8 opening mechanism
9 air conditioner
11 X-ray tube
12 high-voltage power supply
13 cooling water circulator
14 piping
15 heat pump
71 X-ray tube control part
72 heat pump control part
73 temperature control part
151 compressor
152 radiator
153 expansion valve
154 evaporator
155 piping
156 radiator
157 flow rate adjustment part
158 branch pipe
S sample

What is claimed:

1. An X-ray generator for generating X-rays, comprising:
   an X-ray tube;
   a heat pump being used to cool the X-ray tube, waste heat from the heat pump being used to heat a separate part; and
   a processor configured to:
   determine an amount of power supplied to the X-ray tube; and
   control the heat pump based on the amount of power being supplied to the X-ray tube.

2. An X-ray analyzer for analyzing a sample using X-rays, comprising:
   the X-ray generator according to claim 1, wherein the X-rays generated by the X-ray generator are used to analyze the sample.

3. The X-ray analyzer according to claim 2, wherein the separate part comprises a spectroscope for splitting light from a sample;
   wherein waste heat from the heat pump is used to heat the spectroscope.

4. The X-ray analyzer according to claim 3, wherein the waste heat from the heat pump is used to heat another separate part.

5. The X-ray analyzer according to claim 4, wherein the other separate part comprises the sample, wherein waste heat from the heat pump is used to heat the sample.

6. The X-ray generator according to claim 1, wherein the heat pump comprises:
   a compressor that is configured to cool a cooling medium used to cool the X-ray tube; and
   a radiator, that is connected to the compressor via piping, to radiate the waste heat from the compressor to heat the separate part.

7. An X-ray analyzer, comprising:
   an X-ray tube;
   a heat pump that is configured to cool the X-ray tube, wherein waste heat generated from the heat pump is used to heat a spectroscopic chamber of the X-ray analyzer;
   a processor configured to:
   determine an amount of power supplied to the X-ray tube; and
   control the heat pump based on the amount of power being supplied to the X-ray tube.

8. The X-ray analyzer of claim 7, wherein the heat pump comprises:
   a compressor that is configured to provide a heating medium to a radiator via piping; and the radiator that is configured to heat the spectroscopic chamber based on the heating medium being provided via the compressor.

9. The X-ray analyzer of claim 7, further comprising:
a circulator configured to circulate a cooling medium to cool the X-ray tube; wherein
the heat pump is configured to absorb heat from the circulator.

10. The X-ray analyzer of claim 7, wherein the processor is further configured to:
control a driving of a heater of the spectroscopic chamber based on a detection signal from a temperature sensor of the spectroscopic chamber.

11. The X-ray analyzer of claim 7, wherein the processor is further configured to:
control a driving of an opening mechanism of the spectroscopic chamber to adjust a temperature of a spectroscope of the X-ray analyzer based on a detection signal from a temperature sensor of the spectroscopic chamber.

12. The X-ray analyzer of claim 7, wherein the processor is further configured to:
control a driving of an air conditioner of the spectroscopic chamber based on a detection signal from a temperature sensor of the spectroscopic chamber.

13. The X-ray analyzer of claim 7, wherein:
the heat pump comprises a first radiator and a second radiator; and
wherein the processor is further configured to:
adjust a driving of a flow rate adjustment part based on a detection signal from a temperature sensor of the spectroscopic chamber, wherein the flow rate adjustment part
adjusts a flow rate of a cooling medium to the first radiator and another flow rate of the cooling medium to the second radiator.

14. The X-ray analyzer of claim 13, wherein the first radiator is disposed within the spectroscopic chamber, and the second radiator is disposed outside of the spectroscopic chamber.

* * * * *